United States Patent
Lightcap et al.

(10) Patent No.: US 9,921,712 B2
(45) Date of Patent: Mar. 20, 2018

(54) SYSTEM AND METHOD FOR PROVIDING SUBSTANTIALLY STABLE CONTROL OF A SURGICAL TOOL

(71) Applicant: MAKO Surgical Corporation, Ft. Lauderdale, FL (US)

(72) Inventors: Christopher Alan Lightcap, Davie, FL (US); Hyosig Kang, Weston, FL (US); David Gene Bowling, Los Ranchos de Albuquerque, NM (US); John Michael Stuart, Rio Rancho, NM (US); Jerry A. Culp, Kalamazoo, MI (US); Donald W. Malackowski, Schoolcraft, MI (US); Jose Luis Moctezuma de la Barrera, Freiburg (DE); Patrick Roessler, Merzhausen (DE); Joel N. Beer, Albuquerque, NM (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 0 days.

(21) Appl. No.: 15/451,257

(22) Filed: Mar. 6, 2017

(65) Prior Publication Data
US 2017/0177191 A1 Jun. 22, 2017

Related U.S. Application Data

(60) Continuation-in-part of application No. 13/339,369, filed on Dec. 28, 2011, now Pat. No. 9,588,583, and
(Continued)

(51) Int. Cl.
G06F 3/0481 (2013.01)
G06F 3/0484 (2013.01)
(Continued)

(52) U.S. Cl.
CPC .......... *G06F 3/04815* (2013.01); *A61B 34/10* (2016.02); *A61B 34/20* (2016.02);
(Continued)

(58) Field of Classification Search
CPC .. G06F 3/04815; G06F 3/04845; G06F 3/016; G06F 3/01; A61B 34/10; A61B 34/20
See application file for complete search history.

(56) References Cited

U.S. PATENT DOCUMENTS 4,425,818 A  1/1984 Asada et al.
4,442,493 A  4/1984 Wakai et al.
(Continued)

FOREIGN PATENT DOCUMENTS

CN  101031236 A  9/2007
CN  101815981 A  8/2010
(Continued)

OTHER PUBLICATIONS

Ahmadi et al., "Non-Hertzian Contact Stress Analysis for an Elastic Half-Space Normal and Sliding Contact," Int. J. Solids Structures, vol. 19, No. 4, pp. 357-373, 1983.
(Continued)

*Primary Examiner* — Jennifer Mehmood
*Assistant Examiner* — Sardis F Azongha
(74) *Attorney, Agent, or Firm* — Foley & Lardner LLP (57) ABSTRACT

A system for providing substantially stable control of a surgical instrument is provided. The system includes a surgical manipulator for manipulating the surgical instrument and at least one computer configured to identify a first subset and a second subset of interaction geometric primitives associated with a virtual tool; determine, based on the first subset, control forces in a first subspace; and determine based on the second subset, control forces in a second subspace having at least one additional dimension. Control
(Continued)

forces in the additional dimension are only determined based on the second subset of primitives, which is different than the first subset of primitives. The computer is further configured to determine a torque to constrain an orientation of the surgical instrument, wherein determining the torque comprises defining a virtual tool normal and a control plane normal and using the virtual tool normal and control plane normal to calculate the torque.

22 Claims, 5 Drawing Sheets

Related U.S. Application Data a continuation-in-part of application No. 15/401,567, filed on Jan. 9, 2017, which is a continuation of application No. 14/841,062, filed on Aug. 31, 2015, now Pat. No. 9,566,125, which is a division of application No. 13/958,070, filed on Aug. 2, 2013, now Pat. No. 9,119,655.

(60) Provisional application No. 61/428,210, filed on Dec. 29, 2010, provisional application No. 61/679,258, filed on Aug. 3, 2012, provisional application No. 61/792,251, filed on Mar. 15, 2013.

(51) Int. Cl.
G06F 3/01 (2006.01)
A61B 34/20 (2016.01)
A61B 34/10 (2016.01)

(52) U.S. Cl.
CPC .......... *G06F 3/016* (2013.01); *G06F 3/04845* (2013.01); *A61B 2034/107* (2016.02); *A61B 2034/2068* (2016.02)

(56) References Cited

U.S. PATENT DOCUMENTS

| | | |
|---|---|---|
| 4,696,167 A | 9/1987 | Matsui et al. |
| 4,863,133 A | 9/1989 | Bonnell |
| 4,979,949 A | 12/1990 | Matsen et al. |
| 5,078,140 A | 1/1992 | Kwoh |
| 5,086,401 A | 2/1992 | Glassman et al. |
| 5,091,861 A | 2/1992 | Geller et al. |
| 5,154,717 A | 10/1992 | Matsen et al. |
| 5,231,693 A | 7/1993 | Backes et al. |
| 5,279,309 A | 1/1994 | Taylor et al. |
| 5,299,288 A | 3/1994 | Glassman et al. |
| 5,339,799 A | 8/1994 | Kami et al. |
| 5,343,391 A | 8/1994 | Mushabac |
| 5,397,323 A | 3/1995 | Taylor et al. |
| 5,399,951 A | 3/1995 | Lavallee et al. |
| 5,408,409 A | 4/1995 | Glassman et al. |
| 5,434,489 A | 7/1995 | Cheng et al. |
| 5,445,144 A | 8/1995 | Wodicka et al. |
| 5,562,448 A | 10/1996 | Mushabac |
| 5,569,578 A | 10/1996 | Mushabac |
| 5,576,727 A | 11/1996 | Rosenberg et al. |
| 5,629,594 A | 5/1997 | Jacobus et al. |
| 5,630,431 A | 5/1997 | Taylor |
| 5,682,886 A | 11/1997 | Delp et al. |
| 5,689,159 A | 11/1997 | Culp et al. |
| 5,691,898 A | 11/1997 | Rosenberg et al. |
| 5,695,500 A | 12/1997 | Taylor et al. |
| 5,699,038 A | 12/1997 | Ulrich et al. |
| 5,710,870 A | 1/1998 | Ohm et al. |
| 5,711,299 A | 1/1998 | Manwaring et al. |
| 5,721,566 A | 2/1998 | Rosenberg et al. |
| 5,730,129 A | 3/1998 | Darrow et al. |
| 5,731,804 A | 3/1998 | Rosenberg |
| 5,734,373 A | 3/1998 | Rosenberg et al. |
| 5,737,500 A | 4/1998 | Seraji et al. |
| 5,739,811 A | 4/1998 | Rosenberg et al. |
| 5,748,767 A | 5/1998 | Raab |
| 5,762,458 A | 6/1998 | Wang et al. |
| 5,767,648 A | 6/1998 | Morel et al. |
| 5,767,839 A | 6/1998 | Rosenberg |
| 5,769,092 A | 6/1998 | Williamson, Jr. |
| 5,769,640 A | 6/1998 | Jacobus et al. |
| 5,776,136 A | 7/1998 | Sahay et al. |
| 5,784,542 A | 7/1998 | Ohm et al. |
| 5,789,890 A | 8/1998 | Genov et al. |
| 5,792,135 A | 8/1998 | Madhani et al. |
| 5,792,147 A | 8/1998 | Evans et al. |
| 5,806,518 A | 9/1998 | Mittelstadt |
| 5,807,377 A | 9/1998 | Madhani et al. |
| 5,815,640 A | 9/1998 | Wang et al. |
| 5,820,623 A | 10/1998 | Ng |
| 5,824,085 A | 10/1998 | Sahay et al. |
| 5,831,408 A | 11/1998 | Jacobus et al. |
| 5,841,950 A | 11/1998 | Wang et al. |
| 5,847,528 A | 12/1998 | Hui et al. |
| 5,855,553 A | 1/1999 | Tajima et al. |
| 5,855,583 A | 1/1999 | Wang et al. |
| 5,871,018 A | 2/1999 | Delp et al. |
| 5,880,976 A | 3/1999 | Digioia, III et al. |
| 5,882,206 A | 3/1999 | Gillio |
| 5,891,157 A | 4/1999 | Day et al. |
| 5,907,487 A | 5/1999 | Rosenberg et al. |
| 5,907,664 A | 5/1999 | Wang et al. |
| 5,929,607 A | 7/1999 | Rosenberg et al. |
| 5,950,629 A | 9/1999 | Taylor et al. |
| 5,952,796 A | 9/1999 | Colgate et al. |
| 5,959,613 A | 9/1999 | Rosenberg et al. |
| 5,966,305 A | 10/1999 | Watari et al. |
| 5,971,976 A | 10/1999 | Wang et al. |
| 5,976,156 A | 11/1999 | Taylor et al. |
| 5,993,338 A | 11/1999 | Kato et al. |
| 5,995,738 A | 11/1999 | Digioia et al. |
| 5,999,168 A | 12/1999 | Rosenberg et al. |
| 6,002,859 A | 12/1999 | Digioia, III et al. |
| 6,020,876 A | 2/2000 | Rosenberg et al. |
| 6,024,576 A | 2/2000 | Bevirt et al. |
| 6,033,415 A | 3/2000 | Mittelstadt et al. |
| 6,037,927 A | 3/2000 | Rosenberg |
| 6,046,727 A | 4/2000 | Rosenberg et al. |
| 6,050,718 A | 4/2000 | Schena et al. |
| 6,063,095 A | 5/2000 | Wang et al. |
| 6,067,077 A | 5/2000 | Martin et al. |
| 6,084,587 A | 7/2000 | Tarr et al. |
| 6,097,168 A | 8/2000 | Katoh et al. |
| 6,102,850 A | 8/2000 | Wang et al. |
| 6,111,577 A | 8/2000 | Zilles et al. |
| 6,124,693 A | 9/2000 | Okanda et al. |
| 6,157,873 A | 12/2000 | Decamp et al. |
| 6,163,124 A | 12/2000 | Ito et al. |
| 6,181,096 B1 | 1/2001 | Hashimoto et al. |
| 6,191,796 B1 | 2/2001 | Tarr |
| 6,205,411 B1 | 3/2001 | Digioia, III et al. |
| 6,228,089 B1 | 5/2001 | Wahrburg |
| 6,233,504 B1 | 5/2001 | Das et al. |
| 6,236,875 B1 | 5/2001 | Bucholz et al. |
| 6,236,906 B1 | 5/2001 | Muller |
| 6,278,902 B1 | 8/2001 | Hashimoto et al. |
| 6,281,651 B1 | 8/2001 | Haanpaa et al. |
| 6,300,937 B1 | 10/2001 | Rosenberg |
| 6,304,050 B1 | 10/2001 | Skaar et al. |
| 6,311,100 B1 | 10/2001 | Sarma et al. |
| 6,314,312 B1 | 11/2001 | Wessels et al. |
| 6,322,567 B1 | 11/2001 | Mittelstadt et al. |
| 6,325,808 B1 | 12/2001 | Bernard et al. |
| 6,329,777 B1 | 12/2001 | Itabashi et al. |
| 6,329,778 B1 | 12/2001 | Culp et al. |
| 6,330,837 B1 | 12/2001 | Charles et al. |
| 6,336,931 B1 | 1/2002 | Hsu et al. |
| 6,339,735 B1 | 1/2002 | Peless et al. |
| 6,341,231 B1 | 1/2002 | Ferre et al. |
| 6,342,880 B2 | 1/2002 | Rosenberg et al. |
| 6,347,240 B1 | 2/2002 | Foley et al. |
| 6,351,659 B1 | 2/2002 | Vilsmeier |

(56) References Cited

U.S. PATENT DOCUMENTS

| | | |
|---|---|---|
| 6,351,661 B1 | 2/2002 | Cosman |
| 6,352,532 B1 | 3/2002 | Kramer et al. |
| 6,366,272 B1 | 4/2002 | Rosenberg et al. |
| 6,368,330 B1 | 4/2002 | Hynes et al. |
| 6,369,834 B1 | 4/2002 | Zilles et al. |
| 6,377,839 B1 | 4/2002 | Kalfas et al. |
| 6,385,475 B1 | 5/2002 | Cinquin et al. |
| 6,385,508 B1 | 5/2002 | McGee et al. |
| 6,385,509 B2 | 5/2002 | Das et al. |
| 6,401,006 B1 | 6/2002 | Mizuno et al. |
| 6,405,072 B1 | 6/2002 | Cosman |
| 6,408,253 B2 | 6/2002 | Rosenberg et al. |
| 6,411,276 B1 | 6/2002 | Braun et al. |
| 6,413,264 B1 | 7/2002 | Jensen et al. |
| 6,414,711 B2 | 7/2002 | Arimatsu et al. |
| 6,417,638 B1 | 7/2002 | Guy et al. |
| 6,421,048 B1 | 7/2002 | Shih et al. |
| 6,423,077 B2 | 7/2002 | Carol et al. |
| 6,424,356 B2 | 7/2002 | Chang et al. |
| 6,430,434 B1 | 8/2002 | Mittelstadt |
| 6,432,112 B2 | 8/2002 | Brock et al. |
| 6,434,415 B1 | 8/2002 | Foley et al. |
| 6,436,107 B1 | 8/2002 | Wang et al. |
| 6,443,894 B1 | 9/2002 | Sumanaweera et al. |
| 6,450,978 B1 | 9/2002 | Brosseau et al. |
| 6,461,372 B1 | 10/2002 | Jensen et al. |
| 6,463,360 B1 | 10/2002 | Terada et al. |
| 6,466,815 B1 | 10/2002 | Saito et al. |
| 6,468,265 B1 | 10/2002 | Evans et al. |
| 6,473,635 B1 | 10/2002 | Rasche |
| 6,486,872 B2 | 11/2002 | Rosenberg et al. |
| 6,490,467 B1 | 12/2002 | Bucholz et al. |
| 6,491,702 B2 | 12/2002 | Heilbrun et al. |
| 6,494,882 B1 | 12/2002 | Lebouitz et al. |
| 6,501,997 B1 | 12/2002 | Kakino |
| 6,507,165 B2 | 1/2003 | Kato et al. |
| 6,507,773 B2 | 1/2003 | Parker et al. |
| 6,514,082 B2 | 2/2003 | Kaufman et al. |
| 6,520,228 B1 | 2/2003 | Kennedy et al. |
| 6,522,906 B1 | 2/2003 | Salisbury et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,562,055 B2 | 5/2003 | Walen |
| 6,620,174 B2 | 9/2003 | Jensen et al. |
| 6,636,161 B2 | 10/2003 | Rosenberg |
| 6,639,581 B1 | 10/2003 | Moore et al. |
| 6,665,554 B1 | 12/2003 | Charles et al. |
| 6,671,651 B2 | 12/2003 | Goodwin et al. |
| 6,676,669 B2 | 1/2004 | Charles et al. |
| 6,697,048 B2 | 2/2004 | Rosenberg et al. |
| 6,699,177 B1 | 3/2004 | Wang et al. |
| 6,702,805 B1 | 3/2004 | Stuart |
| 6,704,002 B1 | 3/2004 | Martin et al. |
| 6,704,683 B1 | 3/2004 | Hasser |
| 6,704,694 B1 | 3/2004 | Basdogan et al. |
| 6,711,432 B1 | 3/2004 | Krause et al. |
| 6,723,106 B1 | 4/2004 | Charles et al. |
| 6,728,599 B2 | 4/2004 | Wang et al. |
| 6,756,761 B2 | 6/2004 | Takahashi et al. |
| 6,757,582 B2 | 6/2004 | Brisson et al. |
| 6,778,850 B1 | 8/2004 | Adler et al. |
| 6,778,867 B1 | 8/2004 | Ziegler et al. |
| 6,781,569 B1 | 8/2004 | Gregorio et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,799,106 B2 | 9/2004 | Fukushima et al. |
| 6,804,547 B2 | 10/2004 | Pelzer et al. |
| 6,810,314 B2 | 10/2004 | Tashiro et al. |
| 6,827,723 B2 | 12/2004 | Carson |
| 6,832,119 B2 | 12/2004 | Miller |
| 6,833,846 B2 | 12/2004 | Hasser |
| 6,837,892 B2 | 1/2005 | Shoham |
| 6,856,888 B2 | 2/2005 | Kawai |
| 6,871,117 B2 | 3/2005 | Wang et al. |
| 6,892,110 B2 | 5/2005 | Inoue et al. |
| 6,892,112 B2 | 5/2005 | Wang et al. |
| 6,892,129 B2 | 5/2005 | Miyano |
| 6,895,306 B2 | 5/2005 | Ebisawa et al. |
| 6,903,721 B2 | 6/2005 | Braun et al. |
| 6,904,823 B2 | 6/2005 | Levin et al. |
| 6,941,224 B2 | 9/2005 | Fukuyasu |
| 6,958,752 B2 | 10/2005 | Jennings et al. |
| 6,963,792 B1 | 11/2005 | Green |
| 6,978,166 B2 | 12/2005 | Foley et al. |
| 6,982,700 B2 | 1/2006 | Rosenberg et al. |
| 6,999,852 B2 | 2/2006 | Green |
| 7,003,368 B2 | 2/2006 | Koike et al. |
| 7,006,895 B2 | 2/2006 | Green |
| 7,030,585 B2 | 4/2006 | Iwashita et al. |
| 7,034,491 B2 | 4/2006 | Kozai et al. |
| 7,035,711 B2 | 4/2006 | Watanabe et al. |
| 7,035,716 B2 | 4/2006 | Harris et al. |
| 7,038,657 B2 | 5/2006 | Rosenberg et al. |
| 7,042,175 B2 | 5/2006 | Watanabe |
| 7,044,039 B2 | 5/2006 | Powell |
| 7,047,117 B2 | 5/2006 | Akiyama et al. |
| 7,055,789 B2 | 6/2006 | Libbey et al. |
| 7,056,123 B2 | 6/2006 | Gregorio et al. |
| 7,084,596 B2 | 8/2006 | Iwashita et al. |
| 7,084,867 B1 * | 8/2006 | Ho .................... G06F 3/016 |
| | | 345/419 |
| 7,086,056 B2 | 8/2006 | Fukushima |
| 7,092,791 B2 | 8/2006 | Terada et al. |
| 7,097,640 B2 | 8/2006 | Wang et al. |
| 7,102,314 B2 | 9/2006 | Hayashi |
| 7,102,635 B2 | 9/2006 | Shin et al. |
| 7,103,499 B2 | 9/2006 | Goodwin et al. |
| 7,139,601 B2 | 11/2006 | Bucholz et al. |
| 7,155,316 B2 | 12/2006 | Sutherland et al. |
| 7,181,315 B2 | 2/2007 | Watanabe et al. |
| 7,193,607 B2 | 3/2007 | Moore et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,209,117 B2 | 4/2007 | Rosenberg et al. |
| 7,215,326 B2 | 5/2007 | Rosenberg |
| 7,221,983 B2 | 5/2007 | Watanabe et al. |
| 7,225,404 B1 | 5/2007 | Zilles et al. |
| 7,239,940 B2 | 7/2007 | Wang et al. |
| 7,245,202 B2 | 7/2007 | Levin |
| 7,249,951 B2 | 7/2007 | Bevirt et al. |
| 7,260,437 B2 | 8/2007 | Senoo et al. |
| 7,260,733 B2 | 8/2007 | Ichikawa et al. |
| 7,280,095 B2 | 10/2007 | Grant |
| 7,283,120 B2 | 10/2007 | Grant |
| 7,319,466 B1 | 1/2008 | Tarr et al. |
| 7,346,417 B2 | 3/2008 | Luth et al. |
| 7,404,716 B2 | 7/2008 | Gregorio et al. |
| 7,422,582 B2 | 9/2008 | Malackowski et al. |
| 7,447,604 B2 | 11/2008 | Braun et al. |
| 7,454,268 B2 | 11/2008 | Jinno |
| 7,460,104 B2 | 12/2008 | Rosenberg |
| 7,460,105 B2 | 12/2008 | Rosenberg et al. |
| 7,466,303 B2 | 12/2008 | Yi et al. |
| 7,468,594 B2 | 12/2008 | Svensson et al. |
| 7,491,198 B2 | 2/2009 | Kockro |
| 7,542,826 B2 | 6/2009 | Hanzawa |
| 7,543,588 B2 | 6/2009 | Wang et al. |
| 7,573,461 B2 | 8/2009 | Rosenberg |
| 7,577,504 B2 | 8/2009 | Sawada et al. |
| 7,590,458 B2 | 9/2009 | Endo et al. |
| 7,625,383 B2 | 12/2009 | Charles et al. |
| 7,648,513 B2 | 1/2010 | Green et al. |
| 7,657,356 B2 | 2/2010 | Iwashita et al. |
| 7,660,623 B2 | 2/2010 | Hunter et al. |
| 7,667,687 B2 | 2/2010 | Cruz-Hernandez et al. |
| 7,683,565 B2 | 3/2010 | Quaid et al. |
| 7,714,836 B2 | 5/2010 | Rodomista et al. |
| 7,725,162 B2 | 5/2010 | Malackowski et al. |
| 7,742,801 B2 | 6/2010 | Neubauer et al. |
| 7,744,608 B2 | 6/2010 | Lee et al. |

(56) References Cited

U.S. PATENT DOCUMENTS

| | | | |
|---|---|---|---|
| 7,747,311 B2 | 6/2010 | Quaid, III |
| 7,765,890 B2 | 8/2010 | Inoue et al. |
| 7,800,609 B2 | 9/2010 | Tarr et al. |
| 7,813,368 B2 | 10/2010 | Ootaka |
| 7,813,784 B2 | 10/2010 | Marquart et al. |
| 7,813,838 B2 | 10/2010 | Sommer |
| 7,815,644 B2 | 10/2010 | Masini |
| 7,818,044 B2 | 10/2010 | Dukesherer et al. |
| 7,824,424 B2 | 11/2010 | Jensen et al. |
| 7,831,292 B2 | 11/2010 | Quaid et al. |
| 7,835,784 B2 | 11/2010 | Mire et al. |
| 7,843,158 B2 | 11/2010 | Prisco |
| 7,853,356 B2 | 12/2010 | Tsai et al. |
| 7,853,358 B2 | 12/2010 | Joly |
| 7,864,173 B2 | 1/2011 | Handley et al. |
| 7,881,917 B2 | 2/2011 | Nagatsuka et al. |
| 7,892,243 B2 | 2/2011 | Stuart |
| 7,914,522 B2 | 3/2011 | Morley et al. |
| 7,916,121 B2 | 3/2011 | Braun et al. |
| 7,950,306 B2 | 5/2011 | Stuart |
| 7,969,288 B2 | 6/2011 | Braun et al. |
| 8,004,229 B2 | 8/2011 | Nowlin et al. |
| 8,005,571 B2 | 8/2011 | Sutherland et al. |
| 8,005,659 B2 | 8/2011 | Nelson et al. |
| 8,010,180 B2 | 8/2011 | Quaid et al. |
| 8,013,847 B2 | 9/2011 | Anastas |
| 8,049,457 B2 | 11/2011 | Okita et al. |
| 8,049,734 B2 | 11/2011 | Rosenberg et al. |
| 8,054,028 B2 | 11/2011 | Aoyama et al. |
| 8,090,475 B2 | 1/2012 | Blanc et al. |
| 8,095,200 B2 | 1/2012 | Quaid, III |
| 8,271,134 B2 | 9/2012 | Kato et al. |
| 8,287,522 B2 | 10/2012 | Moses et al. |
| 8,391,954 B2 | 3/2013 | Quaid, III |
| 8,498,744 B2 | 7/2013 | Odermatt et al. |
| 8,560,047 B2 | 10/2013 | Haider et al. |
| 8,571,628 B2 * | 10/2013 | Kang ............... A61N 1/372 600/407 |
| 8,831,779 B2 | 9/2014 | Ortmaier et al. |
| 9,364,291 B2 | 6/2016 | Bellettre et al. |
| 2002/0035321 A1 | 3/2002 | Bucholz et al. |
| 2003/0069591 A1 | 4/2003 | Carson et al. |
| 2003/0208296 A1 | 11/2003 | Brisson et al. |
| 2003/0216816 A1 | 11/2003 | Ito et al. |
| 2004/0010190 A1 | 1/2004 | Shahidi |
| 2004/0024311 A1 * | 2/2004 | Quaid, III ............... A61B 34/20 600/428 |
| 2004/0034283 A1 | 2/2004 | Quaid |
| 2004/0034302 A1 | 2/2004 | Abovitz et al. |
| 2004/0077939 A1 | 4/2004 | Graumann |
| 2004/0106916 A1 * | 6/2004 | Quaid ............... A61B 34/20 606/1 |
| 2004/0128030 A1 | 7/2004 | Nagata et al. |
| 2004/0148036 A1 | 7/2004 | Sunami |
| 2004/0157188 A1 | 8/2004 | Luth et al. |
| 2004/0243147 A1 | 12/2004 | Lipow |
| 2005/0171553 A1 | 8/2005 | Schwarz et al. |
| 2006/0071625 A1 | 4/2006 | Nakata et al. |
| 2006/0091842 A1 | 5/2006 | Nishiyama |
| 2006/0109266 A1 | 5/2006 | Itkowitz et al. |
| 2006/0111813 A1 | 5/2006 | Nishiyama |
| 2006/0142657 A1 * | 6/2006 | Quaid ............... A61N 1/372 600/424 |
| 2006/0155262 A1 | 7/2006 | Kishi et al. |
| 2006/0176242 A1 | 8/2006 | Jaramaz et al. |
| 2006/0257379 A1 | 11/2006 | Giordano et al. |
| 2006/0284587 A1 | 12/2006 | Teshima et al. |
| 2007/0013336 A1 | 1/2007 | Nowlin et al. |
| 2007/0085496 A1 | 4/2007 | Philipp et al. |
| 2007/0249911 A1 | 10/2007 | Simon |
| 2007/0260394 A1 | 11/2007 | Dean |
| 2007/0265527 A1 | 11/2007 | Wohlgemuth |
| 2007/0270685 A1 | 11/2007 | Kang et al. |
| 2007/0287911 A1 | 12/2007 | Haid et al. |
| 2008/0001565 A1 | 1/2008 | Nakashima et al. |
| 2008/0004633 A1 * | 1/2008 | Arata ............... A61B 17/1764 606/130 |
| 2008/0009697 A1 | 1/2008 | Haider et al. |
| 2008/0010706 A1 | 1/2008 | Moses et al. |
| 2008/0058776 A1 | 3/2008 | Jo et al. |
| 2008/0065111 A1 | 3/2008 | Blumenkranz et al. |
| 2008/0077158 A1 | 3/2008 | Haider et al. |
| 2008/0114267 A1 | 5/2008 | Lloyd et al. |
| 2008/0161829 A1 | 7/2008 | Kang |
| 2009/0003975 A1 | 1/2009 | Kuduvalli et al. |
| 2009/0012532 A1 | 1/2009 | Quaid et al. |
| 2009/0043556 A1 | 2/2009 | Axelson et al. |
| 2009/0068620 A1 | 3/2009 | Knobel et al. |
| 2009/0082784 A1 | 3/2009 | Meissner et al. |
| 2009/0088774 A1 | 4/2009 | Swarup et al. |
| 2009/0096148 A1 | 4/2009 | Usui |
| 2009/0099680 A1 | 4/2009 | Usui |
| 2009/0102767 A1 | 4/2009 | Shiomi |
| 2009/0112316 A1 | 4/2009 | Umemoto et al. |
| 2009/0149867 A1 | 6/2009 | Glozman et al. |
| 2009/0245992 A1 | 10/2009 | Kato |
| 2009/0248038 A1 | 10/2009 | Blumenkranz et al. |
| 2009/0259412 A1 | 10/2009 | Brogardh |
| 2009/0308683 A1 | 12/2009 | Suzuki |
| 2010/0076474 A1 | 3/2010 | Yates et al. |
| 2010/0094312 A1 | 4/2010 | Morales et al. |
| 2010/0137882 A1 | 6/2010 | Quaid, III |
| 2010/0154578 A1 | 6/2010 | Duval |
| 2010/0168950 A1 | 7/2010 | Nagano |
| 2010/0174410 A1 | 7/2010 | Greer et al. |
| 2010/0286826 A1 | 11/2010 | Tsusaka et al. |
| 2010/0292707 A1 | 11/2010 | Ortmaier et al. |
| 2010/0331859 A1 | 12/2010 | Omori |
| 2011/0077590 A1 | 3/2011 | Plicchi et al. |
| 2011/0082468 A1 | 4/2011 | Hagag et al. |
| 2011/0106102 A1 | 5/2011 | Balicki et al. |
| 2011/0118751 A1 | 5/2011 | Balaji et al. |
| 2011/0130761 A1 | 6/2011 | Plaskos et al. |
| 2011/0152676 A1 | 6/2011 | Groszmann et al. |
| 2011/0160745 A1 | 6/2011 | Fielding et al. |
| 2011/0257653 A1 | 10/2011 | Hughes et al. |
| 2011/0263971 A1 | 10/2011 | Nikou et al. |
| 2011/0264107 A1 | 10/2011 | Nikou et al. |
| 2011/0264112 A1 | 10/2011 | Nowlin et al. |
| 2011/0277580 A1 | 11/2011 | Cooper et al. |
| 2011/0295268 A1 | 12/2011 | Roelle et al. |
| 2011/0301500 A1 | 12/2011 | Maguire et al. |
| 2011/0306985 A1 | 12/2011 | Inoue et al. |
| 2012/0059378 A1 | 3/2012 | Farrell |
| 2012/0071752 A1 | 3/2012 | Sewell et al. |
| 2012/0071893 A1 | 3/2012 | Smith et al. |
| 2012/0123441 A1 | 5/2012 | Au et al. |
| 2012/0143084 A1 | 6/2012 | Shoham |
| 2012/0173021 A1 | 7/2012 | Tsusaka |
| 2012/0197182 A1 | 8/2012 | Millman et al. |
| 2012/0245595 A1 | 9/2012 | Kesavadas et al. |
| 2012/0330429 A1 | 12/2012 | Axelson et al. |
| 2013/0006267 A1 | 1/2013 | Odermatt et al. |
| 2013/0019883 A1 | 1/2013 | Worm et al. |
| 2013/0035690 A1 | 2/2013 | Mittelstadt et al. |
| 2013/0035696 A1 | 2/2013 | Qutub |
| 2013/0060278 A1 | 3/2013 | Bozung et al. |
| 2013/0096574 A1 | 4/2013 | Kang et al. |
| 2013/0116706 A1 | 5/2013 | Lee et al. |
| 2013/0172902 A1 | 7/2013 | Lightcap et al. |
| 2013/0172905 A1 * | 7/2013 | Iorgulescu ............ A61B 17/17 606/130 |
| 2013/0178868 A1 | 7/2013 | Roh |
| 2013/0304258 A1 | 11/2013 | Taylor et al. |
| 2013/0325029 A1 | 12/2013 | Hourtash et al. |
| 2013/0345718 A1 | 12/2013 | Crawford et al. |
| 2014/0135795 A1 | 5/2014 | Yanagihara |
| 2014/0148818 A1 | 5/2014 | Komuro et al. |
| 2014/0195205 A1 | 7/2014 | Benker et al. |

FOREIGN PATENT DOCUMENTS

| | | |
|---|---|---|
| EP | 1 680 007 A2 | 7/2006 |
| EP | 1 871 267 A2 | 1/2008 |

(56) References Cited

FOREIGN PATENT DOCUMENTS

| | | |
|---|---|---|
| EP | 1 973 487 A2 | 1/2008 |
| EP | 2 666 428 | 11/2013 |
| WO | WO-96/11624 A2 | 4/1996 |
| WO | WO-99/37220 A1 | 7/1999 |
| WO | WO-00/21450 A1 | 4/2000 |
| WO | WO-00/35366 A1 | 6/2000 |
| WO | WO-00/59397 A1 | 10/2000 |
| WO | WO-00/60571 A1 | 10/2000 |
| WO | WO-02/00131 A1 | 1/2002 |
| WO | WO-02/24051 A2 | 3/2002 |
| WO | WO-02/060653 A2 | 8/2002 |
| WO | WO-02/065931 A1 | 8/2002 |
| WO | WO-02/074500 A2 | 9/2002 |
| WO | WO-02/076302 | 10/2002 |
| WO | WO-03/086714 A2 | 10/2003 |
| WO | WO-03/094108 A1 | 11/2003 |
| WO | WO-2004/001569 A2 | 12/2003 |
| WO | WO-2004/014244 | 2/2004 |
| WO | WO-2004/019785 | 3/2004 |
| WO | WO-2004/069036 A2 | 8/2004 |
| WO | WO-2005/009215 A2 | 2/2005 |
| WO | WO-2005/122916 A1 | 12/2005 |
| WO | WO-2006/063156 A1 | 6/2006 |
| WO | WO-2006/058633 A1 | 8/2006 |
| WO | WO-2006/091494 A1 | 8/2006 |
| WO | WO-2007/017642 A1 | 2/2007 |
| WO | WO-2007/111749 A2 | 10/2007 |
| WO | WO-2007/117297 A2 | 10/2007 |
| WO | WO-2007/136739 A2 | 11/2007 |
| WO | WO-2007/136768 A2 | 11/2007 |
| WO | WO-2007/136769 A2 | 11/2007 |
| WO | WO-2007/136771 A2 | 11/2007 |
| WO | WO-2009/059330 A2 | 5/2009 |
| WO | WO-2011/021192 A2 | 2/2011 |
| WO | WO-2011/088541 A1 | 7/2011 |
| WO | WO-2011/106861 A1 | 9/2011 |
| WO | WO-2011/113483 A1 | 9/2011 |
| WO | WO-2011/128766 A1 | 10/2011 |
| WO | WO-2011/133873 A1 | 10/2011 |
| WO | WO-2011/133927 A1 | 10/2011 |
| WO | WO-2011/134083 A1 | 11/2011 |
| WO | WO-2012/018816 A2 | 2/2012 |
| WO | WO-2013/181507 A1 | 12/2013 |

OTHER PUBLICATIONS

Ansar et al., "Visual and haptic collaborative tele-presence," Computers & Graphics, vol. 25, 2001, pp. 789-798.

B. Davies, "A review of robotics in surgery", Proceedings of the Institution of Mechanical Engineers, Part H: Journal of Engineering in Medicine Jan. 1, 2000, vol. 214, No. 1, pp. 129-14.

B. Davies, "Computer-assisted and robotics surgery," International Congress and Symposium Series, 1997, pp. 71-82.

B. Preising et al., "A Literature Review Robots in Medicine, Engineering in Medicine and Biology Magazine", IEEE (vol. 10, Issue: 2), Jun. 1991, pp. 13-22, IEEE; 10 pages.

B.L. Davies, "Robotics in minimally invasive surgery, Through the Keyhole: Microengineering in Minimally Invasive Surgery," IEEE Colloquium on Jun. 6, 1995, pp. 5/1-5/2.

Bærentzen, J.A., "Octree-based vol. Sculpting, Proc. Late Breaking Hot Topics," IEEE Visualization '98, 1998, pp. 9-12.

Bainville, et al., Concepts and Methods of Registration for Computer-Integrated Surgery, Computer Assisted Orthopedic Surgery (CAOS), 1999, Hogrefe & Huber Publishers, 22 pages.

Bargar et al., "Primary and Revision Total Hip Replacement Using the Robodoc System," Clinical Orthopaedics and Related Research, No. 354, Sep. 1998, pp. 82-91.

Bei et al., "Multibody Dynamic Simulation of Knee Contact Mechanics," Medical Engineering & Physics, vol. 26, pp. 777-789, 2004.

Bouazza-Marouf et al., "Robot-assisted invasive orthopaedic surgery," Mechatronics in Surgery, vol. 6, issue 4, Jun. 1996, pp. 381-397.

Brandt et al., "CRIGOS: A Compact Robot for Image-Guided Orthopedic Surgery," Information Technology in Biomedicine, IEEE Transactions on, vol. 3, No. 4, 1999, pp. 252-260.

Brisson et al., "Precision Freehand Sculpting of Bone," Medical Image Computing and Computer-Assisted Intervention—MICCAI 2004, Lecture Notes in Computer Science, vol. 3217, 2004, pp. 105-112.

Burghart et al., "Robot Controlled Osteotomy in Craniofacial Surgery," , First International Workshop on Haptic Devices in Medical Applications Proceedings, Jun. 23, 1999, pp. 12-22.

Burghart et al., "Robotergestutzte Osteotomie in der craniofacialen Chirurgie (Robot Clipped osteotomy in craniofacial surgery)," Jul. 1, 1999, 250 pages.

Catto et al., "Iterative Dynamics with Temporal Coherence," Feb. 2005, 24 pages.

Catto, "Soft Constraints Reinventing the Spring," Game Developer Conference, 2011, 51 pages.

Choi et al., "Flexure-based Manipulator for Active Handheld Microsurgical Instrument, Engineering in Medicine and Biology Society," Proceedings of the 2005 IEEE Engineering in Medicine and Biology 27th Annual Conference of the Digital Object Identifier, 2005, pp. 5085-5088.

Colgate et al., Issues in the Haptic Display of Tool Use, Intelligent Robots and Systems 95.'Human Robot Interaction and Cooperative Robots, Proceedings. 1995 IEEE/RSJ International Conference on, vol. 3, 1995, pp. 140-145.

D. Engel et al., "A Safe Robot System for Craniofacial Surgery", Robotics and Automation, 2001. Proceedings 2001 ICRA. IEEE International Conference on (vol. 2), pp. 2020-2024, IEEE; 5 pages.

Davies et al., "ACROBOT—using robots and surgeons synergistically in knee surgery," Advanced Robotics, ICAR '97. Proceedings., 8th International Conference on, 1997, pp. 173-178.

Davies et al., Active compliance in robotic surgery—the use of force control as a dynamic constraint, Proceedings of the Institution of Mechanical Engineers, Part H: Journal of Engineering in Medicine, vol. 211, Apr. 1, 1997, pp. 285-292.

Davies et al., "Neurobot a special-purpose robot for neurosurgery," Robotics and Automation, 2000. Proceedings. ICRA '00. IEEE International Conference on, vol. 4, 2000, pp. 4103-4108.

Davies, B., et al., "Active-Constraint Robotics for Surgery", Proceedings of the IEEE, vol. 94, No. 9, pp. 1696-1704 (2006).

Delp et al., "Computer Assisted Knee Replacement," Clinical Orthopaedics, vol. 354, Sep. 1998, pp. 49-56.

Digioia et al., "Computer Assisted Orthopaedic Surgery Image Guided and Robotic Assistive Technologies," Clinical Orthopaedics & Related Research, Sep. 1998, vol. 354, pp. 8-16.

Doignon et al., "Segmentation and guidance of multiple rigid objects for intra-operative endoscopic vision," Proceeding WDV'05/WDV'06/ICCV'05/ECCV'06 Proceedings of the 2005/2006 International Conference on Dynamical Vision, 2006, pp. 314-327.

Ellis et al., "A surgical planning and guidance system for high tibial osteotomy," Computer Aided Surgery, vol. 4, Apr. 16, 1999, pp. 264-274.

Fadda et al., "Computer Assisted Planning for Total Knee Arthroplasty," 1997, pp. 619-628.

Fadda et al., "Computer-Assisted Knee Arthroplasty at Rizzoli Institutes," First International Symposium on Medical Robotics and Computer Assisted Surgery, Sep. 22-24, 1994, pp. 26-30.

Fadda et al., "Premiers Pas Vers La Dissectomie et la Realisation de Protheses du Genou a L'Aide de Robots," Innov. Tech. Bio. Med., vol. 13, No. 4, 1992, pp. 394-409.

Fleute et al., "Incorporating a statistically based shape model into a system for computer-assisted anterior cruciate ligament surgery," Medical Image Analysis, vol. 3, No. 3, Oct. 1999, pp. 209222.

Gravel et al., Flexible robotic assembly efforts at Ford Motor Company, Intelligent Control, Proceedings of the 2001 IEEE International Symposium on 2001, pp. 173-182.

Gravel et al., Flexible Robotic Assembly, Measuring the Performance and Intelligence of Systems: Proceedings of the 2000 PerMIS Workshop, NIST Interagency/Internal Report (NISTIR), Aug. 2000, pp. 412-418.

(56) References Cited

OTHER PUBLICATIONS

Grueneis et al., "Clinical Introduction of the Caspar System Problems and Initial Results," 4th International Symposium of Computer Assisted Orthopaedic Surgery, 1999, p. 160.
Haider et al., "Minimally Invasive Total Knee Arthroplasty Surgery Through Navigated Freehand Bone Cutting," Journal of Arthroplasty, vol. 22, No. 4, Jun. 2007, pp. 535-542.
Ham et al., "Accuracy study on the registration of the tibia by means of an intramedullary rod in robot-assisted total knee arthroplasty," Poster Session—Knee Arthroplasty, Orthopaedic Research Society, Mar. 12-50, 2000, p. 450.
Ham et al., "Machining and Accuracy Studies for a Tibial Knee Implant Using a Force-Controlled Robot," Computer Aided Surgery, vol. 3, 1998, pp. 123-133.
Harris et al., "Experiences with Robotic Systems for Knee Surgery," Lecture Notes in Computer Science, vol. 1205, 1997, pp. 757-766.
Harris et al., "Intra-operative Application of a Robotic Knee Surgery System, Medical Image Computing and Computer-Assisted Intervention MICCAI'99," vol. 1679, 1999, pp. 1116-1124.
Haβfeld et al., "Intraoperative Navigation Techniques Accuracy Tests and Clinical Report," In: Computer Assisted Radiology and Surgery (CARS'98), Jun. 1998, pp. 670-675.
Ho et al., "Force Control for Robotic Surgery,", ICAR '95, 1995, pp. 21-32.
Ho et al., "Robot Assisted Knee Surgery Establishing a force control strategy incorporating active motion constraint," IEEE Engineering in Medicine and Biology, vol. 14, No. 3, May/Jun. 1995, pp. 292-300.
Hyosig et al., "Autonomous Suturing using Minimally Invasive Surgical Robots, Control Applications," Proceedings of the 2000 IEEE International Conference on, Sep. 25-27, 2000, pp. 742-747.
Hyosig et al., "EndoBot a Robotic Assistant in Minimally Invasive Surgeries, Robotics and Automation," IEEE International Conference on, vol. 2, 2001, pp. 2031-2036.
International Search Report and Written Opinion issued in corresponding International Application No. PCT/US2011/067202 dated May 7, 2012.
J. T. Lea, "Registration Graphs a Language for Modeling and Analyzing Registration in Image-Guided Surgery," Dec. 1998, 49 pages.
Jakopec et al., "The first clinical application of a "hands-on" robotic knee surgery system," Computer Aided Surgery, vol. 6, issue 6, 2001, pp. 329-339.
Jaramaz et al. "Range of Motion After Total Hip Arthroplasty Experimental Verification of the Analytical Simulator," CVRMed-MRCAS'97, Lecture Notes in Computer Science, Feb. 20, 1997, vol. 1205, pp. 573-582.
Kato et al., "A frameless, armless navigational system for computer-assisted neurosurgery". Technical note, Journal of Neurosurgery, vol. 74, May 1991, pp. 845-849; 5 pages.
Kazanzides et al., "Architecture of a Surgical Robot, Systems, Man and Cybernetics," IEEE International Conference on, vol. 2, 1992, pp. 1624-1629.
Khadem et al., "Comparative Tracking Error Analysis of Five Different Optical Tracking Systems," Computer Aided Surgery, vol. 5, 2000, pp. 98-107.
Kienzle et al., "An Integrated CAD-Robotics System for Total Knee Replacement Surgery, Systems, Man and Cybernetics" IEEE International Conference on, vol. 2, 1992, pp. 1609-1614.
Kienzle et al., "Total Knee Replacement Computer-assisted surgical system uses a calibrated robot" Engineering in Medicine and Biology, vol. 14, issue 3, May 1995, pp. 301-306.
Kim et al., "Haptic interaction and volume modeling techniques for realistic dental simulation", Visual Computers, vol. 22, 2006, pp. 90-98.
Korb et al., "Development and First Patient Trial of a Surgical Robot for Complex Trajectory Milling," Computer Aided Surgery, vol. 8, 2008, pp. 247-258.
Koseki et al., "Robotic assist for MR-guided surgery using leverage and parallelepiped mechanism," Medical Image Computing and Computer-Assisted Intervention -MICCAI 2000, Lecture Notes in Computer Science, 2000, vol. 1935, pp. 940-948.
Kozlowski et al., Automated Force Controlled Assembly Utilizing a Novel Hexapod Robot Manipulator, Automation Congress, 2002, Proceedings of the 5th Biannual World, 2002, pp. 547552, vol. 14, 6 pages.
Lavallee et al., "Computer Assisted Spine Surgery a technique for accurate transpedicular screw fixation using CT data and a 3-D optical localizer," Journal of Image Guided Surgery, 1995, pp. 65-73.
Lea et al., "Registration and immobilization in robot-assisted surgery," Journal of Image Guided Surgery, Computer Aided Surgery, col. 1, No. 2, 1995, pp. 80-87.
Leitner et al., "Computer-Assisted Knee Surgical Total Replacement," Lecture Notes in Computer Science, vol. 1205, 1997, pp. 629-638.
Levison et al., Surgical Navigation for THR A Report on Clinical Trial Utilizing HipNav, MICCAI 2000, LNCS 1935, pp. 1185-1187.
Louhisalmi et al., "Development of a Robotic Surgical Assistant," 1994, pp. 1043-1044.
Maquet et al., "An Automated Cell for Prosthesis Surgery," Robotics World, No. 87, 1999, pp. 30-31.
Matsen et al., "Robotic Assistance in Orthopaedic Surgery a Proof of Principle Using Distal Femoral Arthroplasty," Clinical Orthopaedic Related Research, Nov. 1993, vol. 296, pp. 178-186.
Meng et al., "Remote surgery case robot-assisted teleneurosurgery," Robotics and Automation, 2004. Proceedings. ICRA '04. 2004 IEEE International Conference on, Apr. 26-May 1, 2004, vol. 1, pp. 0819-823.
Moctezuma et al., "A Computer and Robotic Aided Surgery System for Accomplishing Osteotomies", First International Symposium on Medical Robotics and Computer Assisted Surgery, Sep. 22-24, 1994, Pittsburgh, Pennsylvania, US; 6 pages.
Nolte et al., "A Novel Approach to Computer Assisted Spine Surgery", Proc. First International Symposium on Medical Robotics and Computer Assisted Surgery, Pittsburgh, 1994, pp. 323-328; 7 pages.
O'Toole et al., ", Biomechanics for Preoperative Planning and Surgical Simulations in Orthopaedics," Computers in Biology and Medicine, vol. 25, issue 2, Mar. 1995, pp. 183-191.
P. Shinsuk, "Safety Strategies for Human-Robot Interaction in Surgical Environment," SICE-ICASE, 2006. International Joint Conference, Oct. 18-21, 2006, pp. 1769-1773.
Paul et al., "A Surgical Robot for Total Hip Replacement Surgery, International Conference on Robotics and Automation," IEEE, 1992, pp. 606-611.
Paul et al., "Development of a Surgical Robot for Cementless Total Hip Arthroplasty", Clinical Orthopaedics and Related Research, No. 285, Dec. 1992, pp. 57-66.
Paul et al., "Robotic Execution of a Surgical Plan, Systems, Man and Cybernetics, 1992," IEEE International Conference on, Oct. 18-21, 1992, pp. 1621-1623.
Petersik et al., "Realistic Haptic Interaction in volume Sculpting for Surgery Simulation," Surgery Simulation and Soft Tissue Modeling, vol. 2673, Jan. 1, 2003, pp. 194-202.
Quaid et al., "Haptic Information Displays for Computer-Assisted Surgery, Robotics and Automation," IEEE International Conference on, vol. 2, 2002, pp. 2092-2097.
R. Abovitz, "Digital surgery the future of medicine and human-robot symbiotic interaction," Industrial Robot: An International Journal, vol. 28, issue 5, pp. 401-406.
R. Buckingham, "Robotics in surgery a new generation of surgical tools incorporate computer technology and mechanical actuation to give surgeons much finer control than previously possible during some operations," IEEE Review, Sep. 1994, pp. 193-196.
R. Buckingham, Safe Active Robotic Devices for Surgery, Systems, Man and Cybernetics, 1993. Systems Engineering in the Service of Human, Conference Proceedings., International Conference on, Oct. 17-20, 1993, vol. 5, pp. 355-358.
R.A. Abovitz, Human-Interactive Medical Robotics, 2000, pp. 71-72.

(56) References Cited

OTHER PUBLICATIONS

Raczkowsky et al., Ein Robotersystem fur craniomaxillofaciale chirurgische Eingriffe (A robotic system for surgical procedures craniomaxillofaciale), Computer Forsch. Entw, vol. 14, 1999, pp. 24-35.
Redlich et al., "Robot assisted craniofacial surgery first clinical evaluation," Computer Assisted Radiology and Surgery, 1999, pp. 828-833.
Rembold et al., "Surgical Robotics: an Introduction," Journal of Intelligent and Robotic Systems, vol. 30, No. 1, 2001, pp. 1-28.
Riviere et al., "Modeling and Canceling Tremor in Human-Machine Interfaces," Engineering in Medicine and Biology Magazine, vol. 15, issue 3, 1996, pp. 29-36.
Rohling et al., "Comparison of Relative Accuracy Between a Mechanical and an Optical Position Tracker for Image-Guided Neurosurgery," Journal of Image Guided Surgery, vol. 1, No. 4, 1995, pp. 30-34.
S. Lembcke, Realtime Rigid Body Simulation Using Impulses, 2006, 5 pages.
Salisbury et al., "Active Stiffness Control of a Manipulator in Cartesian Coordinates, Decision and Control including the Symposium on Adaptive Processes," IEEE, vol. 19, Dec. 1980, pp. 95-100.
Santos-Munné et al., "A Stereotactic/Robotic System for Pedicle Screw Placement, Interactive Technology and the New Paradigm for Healthcare", (Proceedings of the Medicine Meets Virtual Reality III Conference, San Diego, 1995), pp. 326-333, IOS Press and Ohmsha; 8 pages.
Satava, R.M., "Surgical robotics the early chronicles a personal historical perspective," Surgical Laparoscopic Endoscopic Percutaneous Technology, vol. 12, 2002, pp. 6-16.
Schmidt et al., "EasyGuide Neuro, A New System for Image-Guided Planning, Simulation and Navigation in Neurosurgery," Biomedical Engineering, vol. 40, supplement 1, 1995, pp. 233-234.
Seibold et al., "Prototype of Instrument for Minimally Invasive Surgery with 6-Axis Force Sensing Capability, Robotics and Automation," ICRA 2005. Proceedings of the 2005 IEEE International Conference on, 2005, pp. 498-503.
Siebert et al., "Technique and first clinical results of robot-assisted total knee replacement," The Knee, vol. 9, issue 3, Sep. 2002, pp. 173-180.
Sim et al., "Image-Guided Manipulator Compliant Surgical Planning Methodology for Robotic Skull-Base Surgery, Medical Imaging and Augmented Reality," Proceedings. International Workshop on, 2001, pp. 26-29.
Simon et al., "Accuracy validation in image-guided orthopaedic surgery," In Medical Robotics and Computer Assisted Surgery, 1995, pp. 185-192.
Spencer, E.H., "The ROBODOC Clinical Trial a Robotic Assistant for Total Hip Arthroplasty," Orthopaedic Nursing, vol. 14, issue 1, 1996. pages 9-14.
Spetzger et al., "Frameless Neuronavigation in Modern Neurosurgery, Minimally Invasive Neurosurgery," vol. 38, Dec. 1995, pp. 163-166.

T. Wang et al., "A robotized surgeon assistant", Intelligent Robots and Systems '94. 'Advanced Robotic Systems and the Real World', IROS '94. Proceedings of the IEEE/RSJ/GI International Conference on, Sep. 12-16, 1994, pp. 862-869, vol. 2, IEEE, Munich, Germany; 8 pages.
Taylor et al., ", An Image-directed Robotic System for Hip Replacement Surgery," vol. 8, No. 5, 1990, pp. 111-116.
Taylor et al., "A Model-Based Optimal Planning and Execution System with Active Sensing and Passive Manipulation for Augmentation of Human Precision in Computer-Integrated Surgery, Section 4 Robotic Systems and Task-Level Programming, Experimental Robotics II" The 2nd International Symposium, Lecture Notes in Control and Information Sciences, vol. 190, 1991, pp. 177-195.
Taylor et al., "A Steady-Hand Robotic System for Microsurgical Augmentation", MICCAI99: the Second International Conference on Medical Image Computing and Computer-Assisted Intervention, Cambridge, England, Sep. 19-22, 1999. MICCAI99 Submission #1361999, pp. 1031-1041, Springer-Verlag Berlin Heidelberg; 11 pages.
Taylor et al., "An Image-Directed Robotic System for Precise Orthopaedic Surgery, Robotics and Automation," IEEE Transactions on vol. 10, issue 3, 1994, pp. 261-275.
Tonet Et al., "An Augmented Reality Navigation System for Computer Assisted Arthroscopic Surgery of the Knee, Medical Image Computing and Computer-Assisted Intervention—MICCAI 2000," Lecture Notes in Computer Science, vol. 1935, 2000, pp. 1158-1162.
Troccaz et al., "A passive arm with dynamic constraints a solution to safety problems in medical robotics", Systems, Man and Cybernetics, 1993. 'Systems Engineering in the Service of Humans', Conference Proceedings., International Conference on, Oct. 17-20, 1993, pp. 166-171, vol. 3, IEEE, Le Touquet, FR; 6 pages.
Troccaz et al., "Guiding systems for computer-assisted surgery introducing synergistic devices and discussing the different approaches," Medical Image Analysis, vol. 2, No. 2, 1998, pp. 101-119.
Troccaz et al., Semi-Active Guiding Systems in Surgery. A Two-DOF Prototype of the Passive Arm with Dynamic Constraints (PADyC), Mechatronics, vol. 6, issue 4, Jun. 1996, pp. 399-421.
Watanabe et al., "Three-Dimensional Digitizer (Neuronavigator); New Equipment for Computed Tomography-Guided Stereotaxic Surgery,", Surgical Neurology, vol. 27, issue 6, Jun. 1987, pp. 543-547.
Written Opinion for Application No. PCT/US2013/053451 dated Mar. 19, 2014; 12 pages.
Zilles et al., "A Constraint-Based God-object Method for Haptic Display", Intelligent Robots and Systems 95. 'Human Robot Interaction and Cooperative Robots', Proceedings. 1995 IEEE/RSJ International Conference on, Aug. 5-9, 1995, pp. 146-151, vol. 3, IEEE, MIT, Cambridge, MA, USA; 6 pages.

* cited by examiner

SYSTEM AND METHOD FOR PROVIDING SUBSTANTIALLY STABLE CONTROL OF A SURGICAL TOOL

CROSS-REFERENCE TO RELATED PATENT APPLICATIONS

This application is a continuation in part of U.S. application Ser. No. 13/339,369 filed Dec. 28, 2011, which claims the benefit of and priority to U.S. Provisional Application No. 61/428,210, filed Dec. 29, 2010, both of which are incorporated herein by reference in their entireties.

This application is also a continuation in part of U.S. application Ser. No. 15/401,567 filed Jan. 9, 2017, which is a continuation of U.S. application Ser. No. 14/841,062 filed Aug. 31, 2015 and granted as U.S. Pat. No. 9,566,125, which is a divisional of U.S. application Ser. No. 13/958,070 filed Aug. 2, 2013 and granted as U.S. Pat. No. 9,119,655, which claims the benefit of and priority to U.S. Provisional Application No. 61/679,258 filed Aug. 3, 2012 and U.S. Provisional Application No. 61/792,251 filed Mar. 15, 2013, all of which are incorporated herein by reference in their entireties.

BACKGROUND

The invention relates generally to the field of haptics. Specifically, the invention relates to a system and method for providing substantially stable control in a system using a virtual tool.

The field of haptics relates to, among other things, human interactive devices that provide tactile and/or force feedback to a user to achieve a desired goal. Tactile feedback may include providing a user with tactile sensations such as, for example, vibration. Force feedback may include providing various forms of force to a user, such as a positive force or a resistance to movement.

A common use of haptics is to provide a user of a device with guidance or limits for manipulation of that device. For example, the device may be a robotic system having an object, such as a physical tool, for performing a specified function. The user's manipulation of the physical tool can be guided or limited through the use of haptics to provide feedback to the user during manipulation of the physical tool.

Often such guidance is provided by using a computer to create a virtual environment that effectively guides or limits manipulation of the physical tool. The computer may create an association between the physical tool and a virtual tool (a virtual representation of the physical tool) in the virtual environment. The computer also may construct a haptic object within the virtual environment. The haptic object may provide boundaries for guiding or limiting movement of the virtual tool. For example, when the virtual tool interacts with a boundary of the haptic object, tactile or force feedback may be provided to the user. The guidance or limitation resulting from the interaction between the virtual tool and the haptic object effectively provides guidance or limitation for the user's manipulation of the physical tool.

A specific example of such a robotic system using haptics can be found in computer-assisted surgical systems. In such systems, a physical tool, such as a bone-cutting tool, may be associated with a virtual tool in a virtual environment. A pre-operative surgical plan may be used to identify a region for bone resection, which will then be used to create a haptic object in the virtual environment. For example, the haptic object may represent the boundaries of the bone-resection region. The surgeon will receive tactile or force feedback when the virtual tool interacts with the boundaries of the haptic object. This feedback can assist the surgeon in maintaining the bone-cutting tool with the bone-resection region, according to his/her pre-operative plan.

Feedback is generated based on the interaction of the virtual tool with the haptic object. A fundamental relationship often established for haptics is a linear elastic spring, where the contact force applied by the haptic object may be defined by the spring constant, K, and the displacement into the haptic object, $\Delta x$, such that $$\vec{f} = K \Delta \vec{x}$$

To determine the appropriate feedback, the computer is usually able to determine the interaction between the virtual tool and the haptic object. This interaction is often determined by identifying a single haptic interaction point (HIP) that will represent the location of the virtual tool. For example, a HIP may be defined as the center of a spherical culling tool, as long as the haptic object is offset from a resection depth by the radius of the tool. In such cases, the computer uses the relationship between the HIP and the haptic object to determine the interaction of the virtual tool with the haptic object.

Figure 2:
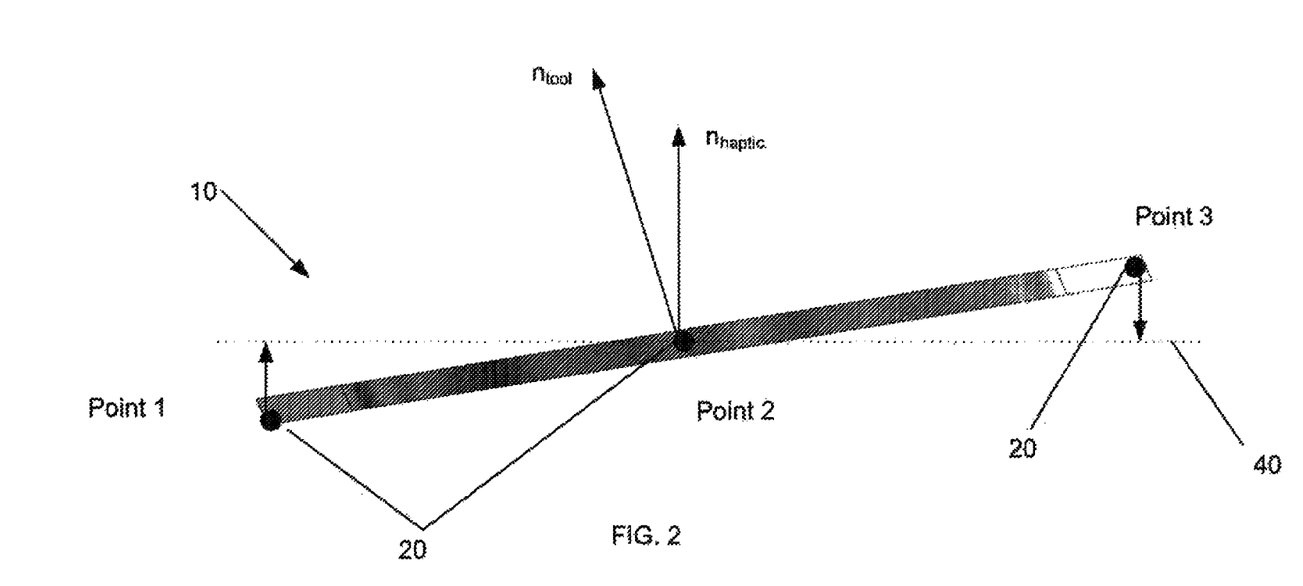
FIG. 2 shows a virtual tool interacting with a boundary of a haptic object.

In certain circumstances, a single HIP may not be fully effective for determining the interaction between the virtual tool and the haptic object. For example, an irregular-shaped virtual tool may not be adequately represented by a single HIP. Due to the irregular shape of the virtual tool, a single HIP may not adequately account for variations on the cutting surface of the tool and/or rotation of the tool. In this case, multiple HIPs may be defined along the con tour of the virtual tool. For example, as shown in FIG. 2, three HIPs 20 (points 1, 2, and 3) may be defined on the outer edge of a virtual tool 10 to provide a better estimation of the interaction between the virtual tool and the haptic object.

Even multiple HIPs may not be fully effective for determining the interaction between the virtual tool and the haptic object. For example, traditional multi-point haptic forces may not be stable because of the competing forces that exist along a bi-lateral constraint such as a plane or line. In the example illustrated in FIG. 2, the irregular-shaped virtual tool 10 has outer HIPs (points 1 and 3) and an inner HIP (point 2). The outer HIPs are in an antagonistic relationship, such that haptic forces determined from the interaction of those outer HIPs (points 1 and 3) with the boundary 40 of the haptic object are in opposite directions, leading to an undesirable oscillation about a haptic plane. This unstable behavior can be attributed to measurement noise, discretization errors, and the competing forces between contact points.

The same unstable behavior may be present in other systems that provide non-haptic force feedback or control of a surgical tool using one or more interaction points.

In view of the foregoing, a need exists for a system and method that can provide substantially stable control for a control object that will correct undesirable oscillation caused by behavior such as measurement noise, discretization errors, and competing forces between interaction/contact points.

SUMMARY

According to an aspect of the present invention, a system for providing substantially stable haptics is provided. The system includes at least one computer configured to identify a first subset and a second subset of haptic interact ion geometric primitives for a virtual tool, determine based on the first subset, haptic forces in a first subspace, and determine based on the second subset, haptic forces in a second subspace different from the first subspace.

According to another aspect of the present invention, a method for providing substantially stable haptics is provided. The method includes the steps of identifying a first subset and a second subset of haptic interaction geometric primitives for a haptic object, determining based on the first subset, by at least one computer, haptic forces for a first subspace, and determining based on the second subset, by at least one computer, haptic forces in a second subspace different from the first subspace.

According to yet another aspect of the present invention, a system for providing substantially stable control of a surgical instrument is provided. The system includes a surgical manipulator for manipulating the surgical instrument and at least one computer. The computer is configured to identify a first subset and a second subset of interaction geometric primitives associated with a virtual tool representing the surgical instrument; determine, based on the first subset, control forces in a first subspace; and determine based on the second subset, control forces in a second subspace having at least one additional dimension to first subspace. Control forces in the additional dimension are only determined based on the second subset of interaction geometric primitives, which is different than the first subset of interaction geometric primitives. The computer is further configured to determine a torque to constrain an orientation of the surgical instrument, wherein determining the torque comprises defining a virtual tool normal and a control plane normal and using the virtual tool normal and control plane normal to calculate the torque.

According to yet another aspect of the present invention, a method for providing substantially stable control of a surgical instrument is provided. The method includes identifying a first subset and a second subset of interaction geometric primitives associated with a virtual tool representing a surgical instrument; determining based on the first subset, by at least one computer, control forces in a first subspace; and determining based on the second subset, by at least one computer, control forces in a second subspace having at least one additional dimension to the first subspace. Control forces in the additional dimension are only determined based on the second subset of interaction geometric primitives, which is different than the first subset of interaction geometric primitives. The method further includes determining a torque to constrain an orientation of the surgical instrument, wherein determining the torque comprises defining a virtual tool normal and a control plane normal and using the virtual tool normal and control plane normal to calculate the torque.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION

Presently preferred embodiments of the invention are illustrated in the drawings. An effort has been made to use the same or like reference numbers throughout the drawings to refer to the same or like parts.

Overview

The present invention relates to a system and method for providing substantially stable control of a tool. According to the present invention, a computer can be used to identify multiple interaction geometric primitives for a virtual tool. To overcome one or more problems in conventional systems, the present invention identifies subsets of the interaction geometric primitives and determines control forces in subspaces corresponding to those subsets. Those control forces may then be used to determine a total interaction force.

Though the present disclosure that follows discusses primarily providing substantially stable haptics, it is to be understood that the following disclosure and calculations can be provided, implemented, and/or utilized by other systems that provide non-haptic force feedback or control of a surgical tool. For example, the following disclosure and force calculations which provide for substantially stable haptics for a haptic system can be similarly applied to a system such as that described in U.S. Pat. No. 9,119,655 entitled "SURGICAL MANIPULATOR CAPABLE OF CONTROLLING A SURGICAL INSTRUMENT IN MULTIPLE MODES" which is incorporated herein by reference in its entirety. The system disclosed in U.S. Pat. No. 9,119,655 provides for control of a surgical tool in a manual and a semi-autonomous mode, which maintains a surgical tool in a proper cutting pattern, path, or area, controlled by forces acting on the tool. The control forces provided by the system can be stabilized according to the teachings and calculations disclosed herein. In this way, references to haptic forces can also be considered to be non-haptic control forces; references to haptic geometric primitives or points can also be considered to be geometric primitives or points; and haptic control can be understood to mean control provided by forces or force feedback, but not specifically haptic control.

In general, a subspace is a set of vectors that is closed under addition and scalar multiplication. For example, geometrically, a subspace of $R^n$ can be a flat through the origin, i.e., a copy of a lower dimensional (or equi-dimensional) Euclidean space sitting in n dimensions. For example, in three-dimensional space $R^3$ there are types of subspaces that can be viewed as different from one another (even though they may overlap), including, without limiting:

(a) lines within $R^3$, which are one-dimensional subspaces of $R^3$;

(b) planes within $R^3$, which are two-dimensional subspaces of $R^3$; and (c) the entire set $R^3$, which is a three-dimensional subspace of itself.

In n-dimensional space $R^n$, there are subspaces of every dimension from 0 to n.

Embodiment of a System for Providing Substantially Stable Haptics

Figure 1:
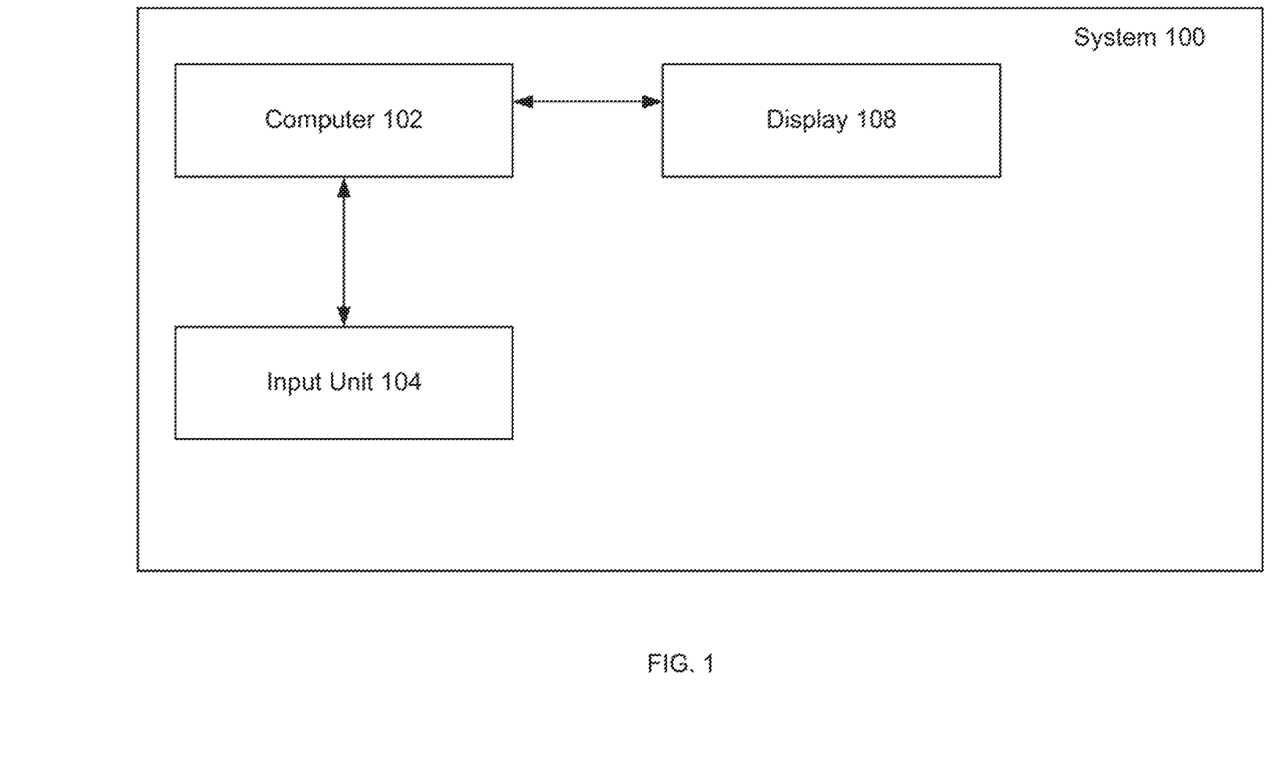
FIG. 1 is a block diagram of a system for providing substantially stable haptics according to the present invention.

FIG. 1 is a block diagram of an embodiment of a computer-assisted system 100 for providing substantially stable haptics. The system includes a computer 102, which is in communication with an input unit 104 and a display 108.

In general, the computer 102 may be configured to determine haptic force(s) based on a virtual tool and, preferably, based on the interaction between a virtual tool and a haptic object. The computer 104 may be configured to, among other things, associate a physical tool with the virtual tool, identify HIGPs for the virtual tool. create the haptic object or objects, determine the interaction between the virtual tool and the haptic object, determine feedback to be provided to the user, and/or control the feedback provided to the user.

The computer 102 may be any known computing system but is preferably a programmable, processor-based system. For example. the computer 102 may include a microprocessor, a hard drive, random access memory (RAM), read only memory (ROM), input/output (I/O) circuitry, and any other well-known computer component. The computer 102 is preferably adapted for use with various types of storage devices (persistent and removable), such as, for example, a portable drive, magnetic storage (e.g., a floppy disk), solid stale storage (e.g., a flash memory card), optical storage (e.g., a compact disc or CD), and/or network/Internet storage. The computer 102 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The input unit 104 enables information to be communicated to the system 100, including the computer 102. The input unit 104 may be one or more devices used for communication of information, such as features of the virtual tool, features of the haptic object, the location of the physical tool, and/or the location of the workpiece upon which the physical tool is or will be working.

The input unit 104 is connected to the computer 102 and may include any device(s) enabling input to a computer. As specific examples, the input unit 104 can include a known input device, such as a keyboard, a mouse. a trackball, a touch screen, a touch pad. voice recognition hardware, dials, switches, buttons, a trackable probe, a foot pedal, a remote control device, a scanner, a camera, a microphone, and/or a joystick. The input unit 104 may also include surgical navigation equipment that provides data to the computer 102. For example, the input unit 104 can include a tracking system for tracking the position of surgical tools and patient anatomy. The tracking system may be, for example, an optical, electromagnetic, radio, acoustic, mechanical, or fiber optic tracking system.

The display 108 is a visual interface between the system 100 and the user. The display 108 enables information to be communicated from the system 100, including the computer 102, to the user. The display 108 may be one or more devices used for communication of information, such as features of the virtual tool, features of the haptic object, and/or the location of the virtual tool relative to the haptic object In some embodiments, the display 108 displays graphical representations of virtual tools and haptic objects in a virtual environment.

The display 108 is connected to the computer 102 and may be any device suitable for displaying text, images, graphics, and/or other visual output. For example, the display 108 may include a standard display screen (e.g., LCD, CRT, plasma, etc.), a touch screen, a wearable display (e.g., eyewear such as glasse5 or goggles), a projection display, a head-mounted display, a holographic display, and for any other visual output device. The display 108 may be disposed on or near the computer 102 (e.g., mounted within a cabinet also comprising the computer 102) or may be remote from the computer 102 (e.g., mounted on a wall of an operating room or other location suitable for viewing by the user). The display 108 is preferably adjustable so that the user can position/reposition the display 108 as needed during a surgical procedure. For example, the display 108 may be disposed on an adjustable arm (not shown) or on any other location well-suited for ease of viewing by the user. The display 108 may be used to display any in formation useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy. tools, implants, etc.), digital or video images, registration information, calibration information, patient data, user data, measurement data, software menus, selection buttons, status information, and the like. The terms model and representation can be used interchangeably to refer to any computerized display of a component (e.g., implant, bone, tissue, etc.) of interest.

This system 100 can be used to determine haptic forces based on a virtual tool. Preferably the system 100 determines the haptic forces based on the interaction between the virtual tool and a haptic object. A specific configuration of a prior system having components that determine haptic forces based on a virtual tool is shown in U.S. Patent Appl. Pub. No. 2009/0012532 A1 to Quaid et al., published Jan. 8, 2009, and assigned to MAKO Surgical Corp., which is hereby incorporated herein by reference in its entirety. That prior system and its components could be modified to be used in accordance with the present invention. The present invention, however, differs from the prior system at least in that the present invention determines haptic forces in a new and advantageous way not contemplated in the prior system. In particular, the present determines the interact ion between the virtual tool and the haptic object using multiple HIGPs for the virtual tool, identifying subsets of the HIGPs, and determining haptic forces in subspaces corresponding to those subsets. Those haptic forces may then be used to determine a total haptic interaction force. A more detailed explanation of the process of determining those haptic forces is provided in the examples below.

Virtual Tool with Haptic Interaction Geometric Primitives (HIGPs)

Figure 3:
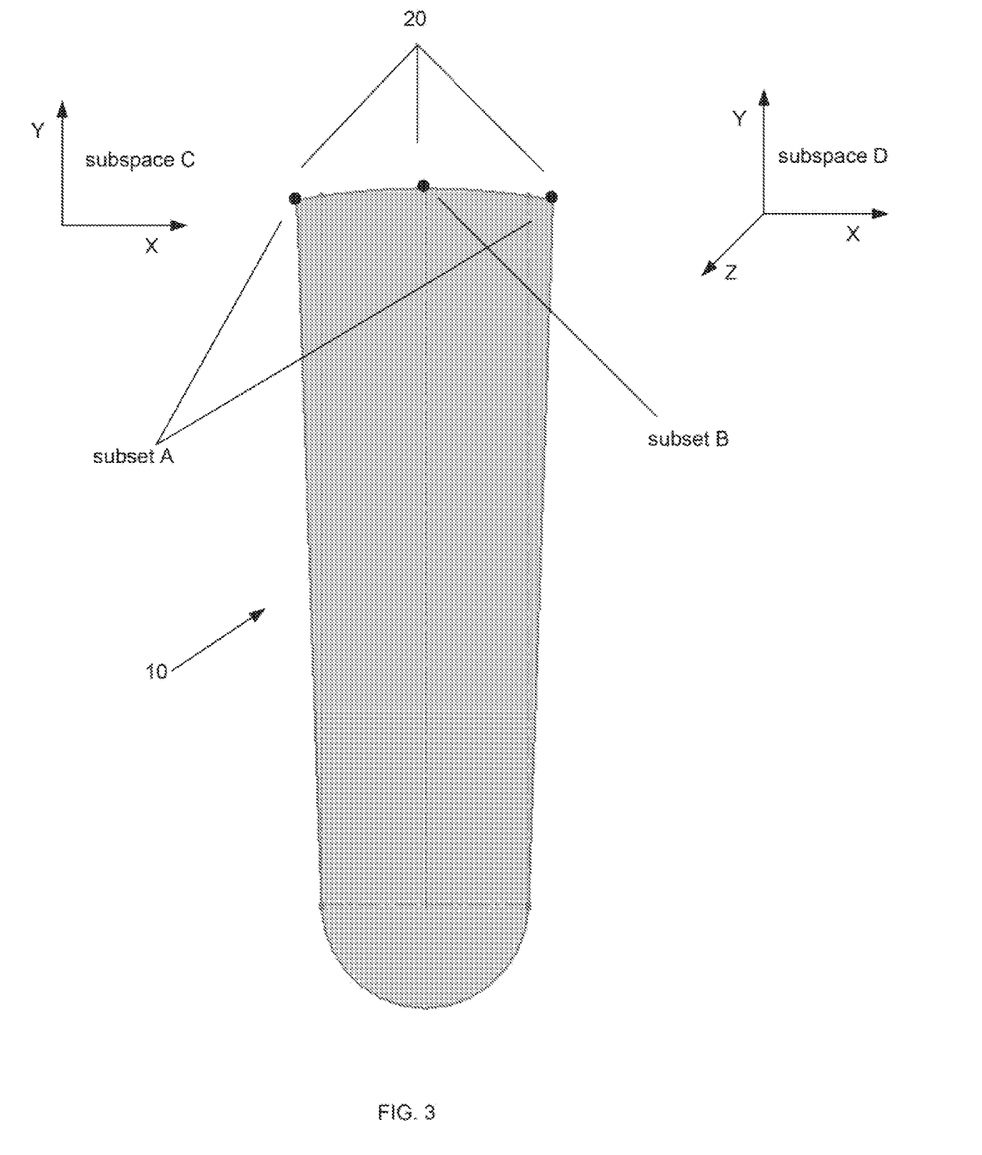
FIG. 3 shows a virtual tool with subsets of haptic interaction points according to an embodiment of the present invention.
Figure 4:
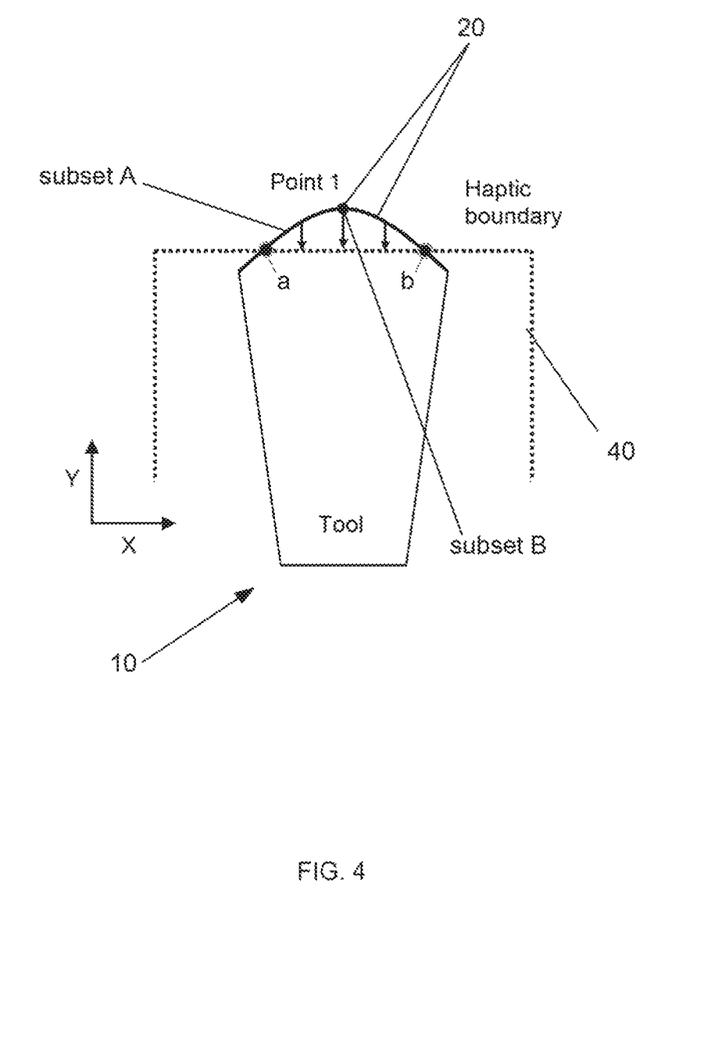
FIG. 4 shows a virtual tool with a haptic interaction arc segment and point according to an embodiment of the present invention.

FIGS. 3 and 4 show an example of an effective area of movement of a virtual tool 10. The virtual tool 10 may represent an object (e.g., surgical tool) in a virtual environment. For example, the virtual tool 10 may represent the manipulation of a physical tool by a user, (e.g., surgeon) to perform a procedure on a patient, such as cutting a surface of a bone in preparation for installing an implant. As the surgeon manipulates the physical tool, the interaction of the virtual tool 10 with a haptic object (not shown) may guide or limit the surgeon by providing haptic (tactile or force) feedback that constrains the physical tool.

As shown in FIGS. 2, 3 and 4, the virtual tool 10 may have one or more haptic interact ion geometric primitives (HIGPs) 20. The HIGPs 20 may correspond to a location on the virtual tool 10 (e.g., a tip of the virtual tool 10). A geometric primitive may be, for example, any one of a point, line, line segment, plane, circle, ellipse, triangle, polygon or curved arc segment. For example, FIGS. 2 and 3 show a virtual tool 10 wherein the HIGPs 20 are points. Alternatively, FIG. 4 shows a virtual tool 10 wherein the HIGPs 20 are an arc segment and a point.

The computer 102 can determine the interaction of the HIGPs 20 of the virtual tool 10 with one or more boundaries of haptic object(s) in a virtual environment. Boundaries 40 of haptic objects are shown, for example, in FIGS. 2 and 4. A haptic object may be a representation of a pre-defined boundary or component. For example, in the computer-assisted system 100, a pre-operative surgical plan may be used to generate a region for bone resection, and a haptic object may be used to constrain the virtual tool 10 to stay inside boundaries 40 of the haptic object that correspond to the boundaries of the bone-resection region. Accordingly, resulting haptic forces me generated to guide a surgeon according to his/her pre-operative plan.

As stated above, when haptic forces are determined from multiple HIGPs 20, competing forces may cause instability. For a given virtual tool 10, the system 100 of the present invention is configured to provide substantially stable haptics by identifying subsets of the HIGPs and determining haptic forces in subspaces corresponding to those subsets, as described in further detail below.

Embodiment Using Points as HIGPs

Figure 5:
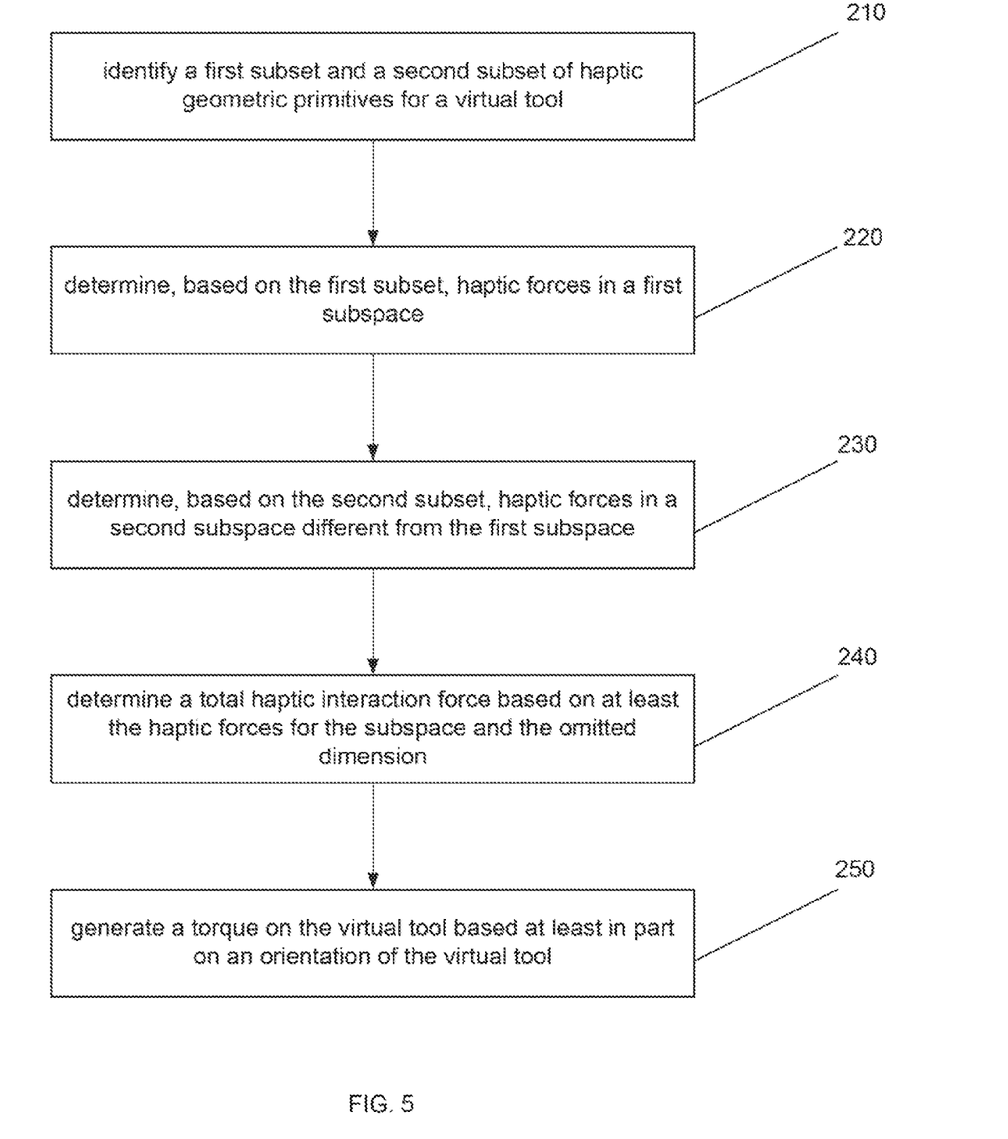
FIG. 5 is a now chart for a method for providing substantially stable haptics according to the present invention.

With reference to FIGS. 2, 3 and 5, an embodiment of a process for providing substantially stable haptics that can be executed by the system 100 will now be described. In this embodiment, the HIGPs 20 for a virtual tool 10 are all points. These HIGPs 20, in the form of points, will be referred to herein as haptic interaction points (HIPs). A plurality of these HIPs 20 may be, for example, disposed along an outer edge of the virtual tool 10. As shown in FIG. 3, HIPs 20 are located along a top edge of the virtual tool 10.

In step 210 of FIG. 5, subsets of HIPs 20 for a virtual tool 10 are identified. FIG. 3 shows a first subset A and a second subset B. The first subset A preferably includes a plurality of HIPs 20. The second subset B preferably includes only one HIP 20, though it may include more. As shown in FIG. 3, the HIP 20 of the second subset B is disposed between HIPs 20 of the first subset A.

In step 220, haptic forces are determined based on the interaction of the first subset A of HIPs 20 with a boundary 40 of a haptic object. The haptic forces are determined in a first subspace that omits at least one dimension. Preferably, as shown in FIG. 3, in a three-dimensional coordinate system $R^3$, the first subspace C is defined in two dimensions $\{x, y\}$ with the third dimension $\{z\}$ being omitted. Haptic forces from HIPs 20 of subset A may be mapped to a subspace C of the special Euclidean group SE(3). Each force acting on HIPs 20 of subset A may be mapped to subspace C using a projection matrix, which is akin to a spatial filter. For example, the projection matrix that maps the force $[f_x, f_y, f_z]^T$ in three-dimensional space $R^3$ to the force $[f_x, f_y, 0]^T$ can be described as $$P = \begin{bmatrix} 1 & 0 & 0 \\ 0 & 1 & 0 \\ 0 & 0 & 0 \end{bmatrix}, \text{ such that } P \begin{bmatrix} fx \\ fy \\ fz \end{bmatrix} = \begin{bmatrix} fx \\ fy \\ 0 \end{bmatrix}$$

The haptic forces determined from the HIPs 20 in subset A are projected onto subspace C. Accordingly, haptic forces determined from the HIPs 20 of subset A in the x and y dimension are determined and haptic forces from the HIPs 20 of subset A in the z dimension are omitted. Mapping haptic forces from each HIP of the first subset in the first subspace assists in stabilizing a virtual tool with multiple HIGPs by eliminating the unstable nature of competing haptic interaction forces.

In step 230, haptic forces from the second subset B of HIPs 20 are determined in a second subspace different from the first subspace. Preferably, as shown in FIG. 3, in a three-dimensional coordinate system, the second subspace D is defined in three dimensions $\{x, y, z\}$ with the third dimension $\{z\}$ (normal to x, y) being the dimension that was omitted in the first subspace C. Accordingly, the haptic forces for the second subset B of HIPs 20 are defined by forces in three dimensions $\{x, y, z\}$ in the second subspace D. As shown in FIG. 3, the z dimension is normal to the x and y dimension. As a result, haptic forces normal to subspace C (in the z dimension) are only defined based on the HIPs 20 in subset B. In the embodiment shown in FIG. 3, subset B includes a single HIP 20 positioned between HIPs 20 of subset A. Thus, the haptic forces normal to subspace C are only defined from the single center HIP 20. Relying solely on the single HIP 20 of subset B to define forces normal to the first subspace C reduces the amount of competing haptic interaction forces, which in t urn increases stability.

In the preferred embodiment discussed above, the first subspace is a two-dimensional subspace of three-dimensional space $R^3$, and the second subspace is a three-dimensional subspace of three-dimensional space $R^3$. However, other subspaces and other n-dimensional spaces may be utilized. Preferably, the first subspace has at least one less dimension than the second subspace. Even more preferably, the first subspace has only one less dimension than the second subspace.

In step 240, a total haptic interaction force is determined, preferably by summing the haptic forces in the first subspace C and the second subspace D. The total haptic interaction force, f, can be a summation of the individual haptic forces, $f_i$, from each HIP 20 in subset A and subset B, and can be described as:

$$\vec{f} = \sum_{i=1}^{n} P_i \vec{f}_i$$

where $P_i$ represents the projection matrix for each particular HIP 20.

In step 250, a torque can be generated to provide a further constraint on the orientation of the virtual tool 10 (and thus the physical tool). Preferably, the torque, $\tau$, may be generated from a tool normal ($\vec{n}_{tool}$) and haptic plane normal ($\vec{n}_{haptic}$) (See FIG. 2) to properly constrain the orientation. For example, $$\vec{\tau} = K\theta(\vec{n}_{tool} \times \vec{n}_{haptic})/\|\vec{n}_{tool} \times \vec{n}_{haptic}\|,$$

where K represents the rotational haptic stiffness, and $\theta$ is the angular displacement.

In addition to generating a torque there are several strategies for reducing the contribution of forces that enable the resultant force to be stable as described in A. Petersik, B. Pflesser, U. Tiede, K. Hohne and R. Leuwer, "Realistic Haptic Interaction in Volume Sculpting for Surgery Simulation", Lecture Notes in Computer Science, vol. 2673, 2003.

Embodiment Using Complex Body as HIGPs

Alternatively, the HIGPs 20 may include other complex bodies, such as a curved arc segment, or may include a combination of complex bodies and point(s). As shown in FIG. 4, both the arc segment and point (point 1) are located along a top edge of the virtual tool 10. The process for providing substantially stable haptics for a virtual tool as shown in FIG. 4 is the same as described above. Preferably in step 210, the arc segment is identified as the first subset (subset A) and the point is identified as the second subset (subset B) of the geometric primitives 20.

In step 220, the resulting forces for the arc segment (subset A) are then mapped to a first subspace of the special Euclidean group SE(3). Here, haptic forces are defined from the resulting interference between the curved arc segment (subset A) and a boundary 40 of a haptic object. As shown in FIG. 4 specifically, haptic forces are determined from the penetration of a non-uniform virtual tool 10 into a boundary 40 (haptic wall). There are multiple elastic contact theories that may be used to estimate contact forces from this displacement, including Hertzian contact models, elastic half-space models (See N. Ahmadi, L. M. Keer, and T. Mura, "Non-Hertzian contact stress analysis for an elastic half-space normal and sliding contact," Int. J. Solids Structures, vol. 19, no. 4, pp. 357-373, 1983.), and elastic foundation models.

In the elastic foundation model, contact forces are approximated through the assumption that the deformation al one location does not influence deformations at all locations throughout the object. See Y. Bei. and B. J. Fregly, "Multibody dynamic simulation of knee contact mechanics," Medical Engineering & Physics, vol. 26, pp. 777-789, 2004. This contact model comprises independent springs evenly-distributed across the contact surface, representing a layer of elastic material. Accordingly, the pressure from any spring element on the surface may be written as $$\vec{p} = \frac{(1-v)E}{(1+v)(1-2v)} \frac{\vec{d}}{h},$$

where E is the spring constant of the elastic layer, $v$ is Poisson's ratio, h is the thickness of the layer, and d is the spring deformation. In this model, the spring deformation is defined as the interpenetration of the undeformed contact surfaces in the direction of the midsurface normal. From this result, haptic forces arising from the penetration of an arc segment 20 into a boundary 40 of a haptic object may be determined through integration, such that $$\vec{f}_i = \int_a^b \vec{p}\, dx,$$

In step 230, haptic forces for point 1 (subset B) are determined in a second subspace different from the first subspace. Preferably, the second subspace is normal to the first subspace. As a result, haptic forces normal to the first subspace are only defined based on point 1.

In step 240, the total haptic force on the virtual tool 10 can be defined from a summation of the individual components projected into the first subspace and second subspace, such that $$\vec{f} = \sum_{i=1}^{n} P_i \vec{f}_i$$

where fi represents the contribution of forces from a particular arc segment, point, or surface. For example, the force f1 may be defined from the penetration of the arc segment in the first subspace, and the force f2 may be defined from the penetration of point 1 in the second subspace, normal to the first subspace.

In step 250, a torque is determined to further constrain the orientation of the virtual tool 10. Preferably, the torque may be generated from a tool normal ($\vec{n}_{tool}$) and haptic plane normal ($\vec{n}_{haptic}$) (See FIG. 2) to properly constrain the orientation of the tool. For example, $$\vec{\tau} = K\theta(\vec{n}_{tool} \times \vec{n}_{haptic})/\|\vec{n}_{tool} \times \vec{n}_{haptic}\|,$$

where K represents the rotational haptic stiffness, and $\theta$ is the angular displacement.

CONCLUSION

The present invention is not limited to the embodiments disclosed above. Those embodiments, however, disclose examples of configurations that can advantageously provide substantially stable haptics by using a computer to identify multiple HIGPs for a virtual tool, identify subsets of the HIGPs, and determine haptic forces in subspaces corresponding to those subsets. Those haptic forces may then be used to determine a total haptic interaction force. Embodiments can be constructed to overcome the instability problems of prior haptic systems. The present invention can be implemented in a wide variety of configurations beyond those disclosed herein.

For example, the above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface. a Web browser through which a user can internet with an example implementation, and/or other graphical user interfaces for a transmitting device. The components of the system can be interconnected by any form or medium of digital data communication {e.g., a communication network).

The system can include clients and servers. A client and n server are generally remote from each other and typically interact through a communication network. The relationship of client and server arises by virtue of computer programs running on the respective computers and having a client-server relationship to each other.

Communication networks can include, for example, the internet, a carrier internet protocol (IP) network (e.g., local area network (LAN), wide area network (WAN), campus area network (CAN), metropolitan area network (MAN), home area network (RAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example the public switched telephone network (PSTN), a private branch exchange (PBX), a wireless network (e.g., RAN, bluetooth, code-division multiple access (CDMA) network, time division multiple access (TOMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft™ Internet Explorer™ available from Microsoft Corporation, Mozilla™ Firefox available from Mozilla Corporation). The mobile computing device includes. for example, a personal digital assistant (PDA).

Other embodiments of the invention will be apparent to those skilled in the art from consideration of the specification and practice of the invention disclosed herein. It is intended that the specification and examples be considered as exemplary only.

What is claimed is:

1. A system for providing substantially stable control of a surgical instrument, comprising:
    a surgical manipulator for manipulating the surgical instrument; and
    at least one computer configured to:
    identify a first subset and a second subset of interaction geometric primitives associated with a virtual tool representing the surgical instrument;
    determine, based on the first subset, control forces in a first subspace;
    determine based on the second subset, control forces in a second subspace having at least one additional dimension to first subspace;
        wherein control forces in the additional dimension are only determined based on the second subset of interaction geometric primitives, which is different than the first subset of interaction geometric primitives; and
    determine a torque to constrain an orientation of the surgical instrument, wherein determining the torque comprises defining a virtual tool normal and a control plane normal and using the virtual tool normal and control plane normal to calculate the torque.

2. The system of claim 1, wherein the first subspace has only one less dimension than the second subspace.

3. The system of claim 1, wherein the first subspace is a two-dimensional subspace of three-dimensional space $R^3$, and the second subspace is a three-dimensional subspace of three-dimensional space $R^3$.

4. The system of claim 1, wherein the at least one computer is configured such that a total interaction force is determined by summing at least the control forces in the first subspace and the control forces in the second subspace.

5. The system of claim 1, wherein the interaction geometric primitives are at least one of a point, line, line segment, plane, circle, ellipse, triangle, polygon and curved arc segment.

6. The system of claim 1, wherein the first subset includes a plurality of interaction geometric primitives.

7. The system of claim 6, wherein the second subset includes only one interaction geometric primitive.

8. The system of claim 7, wherein the interaction geometric primitive of the second subset is disposed between interaction geometric primitives of the first subset.

9. The system of claim 1, wherein the first subset constitutes a non-linear boundary of the virtual tool.

10. The system of claim 1, wherein the at least one computer is configured to determine a torque based at least in part on an orientation of the virtual tool.

11. The system of claim 1, wherein the computer is further configured to selectively operate the surgical manipulator in a first operating mode and a second operating mode.

12. The system of claim 11, wherein the first operating mode is a manual mode and the second operating mode is a semi-autonomous mode.

13. A method for providing substantially stable control of a surgical instrument, comprising:
    identifying a first subset and a second subset of interaction geometric primitives associated with a virtual tool representing a surgical instrument:
    determining based on the first subset, by at least one computer, control forces in a first subspace;
    determining based on the second subset, by at least one computer, control forces in a second subspace having at least one additional dimension to the first subspace;
    wherein control forces in the additional dimension are only determined based on the second subset of interaction geometric primitives, which is different than the first subset of interaction geometric primitives; and
    determining a torque to constrain an orientation of the surgical instrument, wherein determining the torque comprises defining a virtual tool normal and a control plane normal and using the virtual tool normal and control plane normal to calculate the torque.

14. The method of claim 13, wherein the first subspace has only one less dimension than the second subspace.

15. The method of claim 13, wherein the first subspace is a two-dimensional subspace of three-dimensional space $R^3$, and the second subspace is a three-dimensional subspace of three-dimensional space $R^3$.

16. The method of claim 13, further comprising:
    determining, by at least one computer, a total interaction force by summing at least the control forces in the first subspace and the control forces in the second subspace.

17. The method of claim 13, wherein the interaction geometric primitives are at least one of a point, line, line segment, plane, circle, ellipse, triangle, polygon and curved arc segment.

18. The method of claim 13, wherein the first subset includes a plurality of interaction geometric primitives.

19. The method of claim 13, wherein the second subset includes only one interaction geometric primitive.

20. The method of claim 19, wherein the interaction geometric primitive of the second subset is disposed between interaction geometric primitives of the first subset.

21. The method of claim 13, wherein the first subset constitutes a non-linear boundary of the virtual tool.

22. The method of claim 13, further comprising:
    determining a torque based at least in part on an orientation of the virtual tool.

* * * * *